United States Patent
Aechtner et al.

(10) Patent No.: US 12,233,141 B2
(45) Date of Patent: *Feb. 25, 2025

(54) BLEACHING AND COLORING COMPOSITION FOR KERATIN FIBERS COMPRISING DIRECT DYES

(71) Applicant: KAO CORPORATION, Tokyo (JP)

(72) Inventors: Anja Aechtner, Darmstadt (DE); Jonathan Wood, Darmstadt (DE); Marine Delbe, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/044,222

(22) PCT Filed: Sep. 20, 2021

(86) PCT No.: PCT/EP2021/075793
§ 371 (c)(1),
(2) Date: Mar. 7, 2023

(87) PCT Pub. No.: WO2022/069282
PCT Pub. Date: Apr. 7, 2022

(65) Prior Publication Data
US 2023/0372212 A1    Nov. 23, 2023

(30) Foreign Application Priority Data
Sep. 30, 2020  (EP) .................... 20199261

(51) Int. Cl.
| | | |
|---|---|---|
| *A61Q 5/10* | (2006.01) | |
| *A61K 8/22* | (2006.01) | |
| *A61Q 5/08* | (2006.01) | |

(52) U.S. Cl.
CPC ............ *A61K 8/22* (2013.01); *A61Q 5/08* (2013.01); *A61K 2800/31* (2013.01); *A61K 2800/432* (2013.01); *A61K 2800/48* (2013.01)

(58) Field of Classification Search
CPC ............ A61K 8/22; A61K 2800/31; A61K 2800/432; A61K 2800/48; A61K 8/49; A61Q 5/08; A61Q 5/10; A61Q 5/05
USPC .......................................... 8/405
See application file for complete search history.

(56) References Cited

U.S. PATENT DOCUMENTS

| | | | |
|---|---|---|---|
| 2017/0258695 A1* | 9/2017 | Consoli | A61K 8/55 |
| 2017/0290749 A1* | 10/2017 | Borgnini | A61K 8/22 |
| 2017/0354581 A1* | 12/2017 | Consoli | A61Q 5/10 |

FOREIGN PATENT DOCUMENTS

| | | | | |
|---|---|---|---|---|
| EP | 1 366 752 A1 | 12/2003 | | |
| EP | 1 372 581 A1 | 1/2004 | | |
| EP | 2 883 531 A1 | 6/2015 | | |
| EP | 2883535 A1 * | 6/2015 | | A61Q 5/065 |
| EP | 2263642 | 4/2020 | | |
| JP | 2004-524331 A | 8/2004 | | |
| WO | WO 02/074270 A1 | 9/2002 | | |
| WO | WO2019-057829 | 3/2019 | | |

OTHER PUBLICATIONS

Office Action issued May 21, 2024, in corresponding Japanese Patent Application No. 2023-516796 (with English Translation), 7 pages.
International Search Report & Written Opinion mailed on Mar. 7, 2022 in PCT/EP2021/075793 filed on Sep. 20, 2021 (8 pages).
European Search report issued Mar. 9, 2021 in European Application 20199261.7, filed Sep. 30, 2020, 5 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A bleaching and coloring composition for keratin fibers, including one or more alkalizing agents, one or more bleaching compounds, HC Blue 18 and/or a salt thereof, and tetrabromophenol blue and/or a salt thereof. A method for bleaching and coloring of keratin fibers, including mixing the bleaching and coloring composition with a second aqueous composition including hydrogen peroxide as one or more oxidizing agents and having a pH in the range of 1 to 6 to yield a ready-to-use composition having a pH in the range of 7 to 12, applying the ready-to-use composition onto the keratin fibers and leaving it for a time period of 1 to 60 min, and optionally heating the keratin fibers to a temperature in the range of 30° C. to 60° C., and rinsing-off the keratin fibers and optionally drying the keratin fibers.

21 Claims, No Drawings

BLEACHING AND COLORING COMPOSITION FOR KERATIN FIBERS COMPRISING DIRECT DYES

CROSS REFERENCE TO RELATED APPLICATIONS

This application is a National Stage entry under 35 U.S.C. § 371 of PCT/EP2021/075793, filed on Sep. 20, 2021, and claims priority to European Patent Application No. 20199261.7, filed on Sep. 30, 2020. The entire contents of both are incorporated herein by reference.

FIELD OF THE INVENTION

The present invention is directed to bleaching and coloring compositions for keratin fibers. Additionally, a methods for bleaching and coloring and a kit-of-parts is disclosed.

BACKGROUND OF THE INVENTION

Bleaching of keratin fibers is typically desired when customers with dark hair color intend to lighten their hair color. It is also necessary when the customer prefers a color shade that is lighter in comparison to their natural hair color. Thus, it is common to combine bleaching and coloring processes.

For achieving intensive and long-lasting colorations, bleaching processes are combined with dyeing processes. Such a combination is a time-consuming two-step process, because the development of the oxidative hair color after the bleach adds additional process time.

This disadvantage could be avoided when the bleaching and dyeing process take place simultaneously. A class of dyes, which allow for color development without a separate oxidative step, are direct dyes.

Applicant has developed new direct dyes (EP1366752), which complement the availability and color range of the existing ones. A series of the aforementioned developed dyes comprises HC Blue 18, HC Red 18, and HC Yellow 16.

The aforementioned dyes were added to bleaching and dyeing compositions (EP2883531, EP2883531) and improved stability of the dyes in presence of an oxidizable solvent was found.

EP1372581 discloses another direct dye, namely tetrabromophenol blue, in bleaching powder for simultaneously bleaching and dyeing of keratin fibers.

However, especially for customers with dark hair, the bleaching process has an undesired side effect, because the bleached hair appears with a warm yellow to red tone, which is not appreciated and accepted as a natural blond hair color.

Thus, despite the attempts of the prior art, there is a necessity to develop bleaching and coloring compositions, which are perceived as natural colorations without undesired color shifts.

SUMMARY OF THE INVENTION

Therefore, the first object of the present invention is a bleaching and coloring composition for keratin fibers, preferably for human keratin fibers, more preferably for human hair, comprising:
  a) one or more alkalizing agent(s),
  b) one or more bleaching compound(s),
  c) HC Blue 18 and/or its salt(s),
  d) tetrabromophenol blue and/or its salt(s).

The second object of the present invention is a two-part bleaching and coloring composition comprising a first composition as defined above and a second aqueous composition having a pH in the range of 1 to 6 and comprising one or more oxidizing agent(s), preferably hydrogen peroxide.

The third object of the present invention is a method for bleaching and coloring of keratin fibers, preferably human keratin fibers, more preferably human hair comprising the steps of:
  i) mixing the bleaching and coloring composition as defined above with a second aqueous composition comprising one or more oxidizing agent(s), preferably hydrogen peroxide, and having a pH in the range of 1 to 6 to yield a ready-to-use composition having a pH in the range of 7 to 12,
  ii) applying the ready-to-use composition onto keratin fibers and leaving it for a time period of 1 to 60 min, and optionally heating the keratin fibers to a temperature in the range of 30° C. to 60° C.,
  iii) rinsing-off the keratin fibers and optionally drying keratin fibers.

The fourth object of the present invention is a kit-of-part for bleaching and coloring of keratin fibers, preferably human keratin fibers, more preferably human hair, comprising:
  a first composition as defined above,
  a second aqueous composition having a pH in the range of 1 to 6 and comprising one or more oxidizing agent(s), preferably hydrogen peroxide,
  a third composition selected from
  an anhydrous composition comprising one or more oxidizable solvent(s), preferably selected from 2-phenoxyethanol, benzyl alcohol, and/or their mixtures, or
  a composition comprising one or more alkoxylated organopolysiloxane, one or more compound(s) selected from alkoxylated glyceryl ester(s) and/or optionally alkoxylated alkyl glyceryl ether(s), and/or their mixtures, at a total concentration of more than 10% by weight, calculated to the total weight of the third composition, wherein the third composition comprises less than 40% by weight of water, calculated to the total weight of the third composition.

DETAILED DESCRIPTION OF THE INVENTION

Inventors of the present invention have unexpectedly found out that the combination of two blue hair direct dyes, namely HC Blue 18 and tetrabromophenol blue, deliver in combination a strong dyeing result when applied simultaneously with bleaching compounds. Undesired yellow to red tones after the bleaching are avoided and the coloration is intense, bright, and perceived as natural.

Bleaching and Coloring Composition

The present invention is directed to a bleaching and coloring composition for keratin fibers, preferably for human keratin fibers, more preferably for human hair, comprising:
  a) one or more alkalizing agent(s),
  b) one or more bleaching compound(s),
  c) HC Blue 18 and/or its salt(s),
  d) tetrabromophenol blue and/or its salt(s).

Compound(s) According to Group a)

The composition of the present invention comprises one or more alkalizing agent(s) as compound(s) according to a).

It is preferred from the viewpoint of storage stability and bleaching power that one or more compound(s) according to group a) is one or more inorganic alkalizing agent(s), preferably selected from metasilicates, carbonates, and/or bicarbonates, and/or their alkali or earth alkali salts, and/or their mixtures.

Further suitable inorganic alkalizing agent(s) are ammonia salt(s), for example alkali and/or earthalkaline salt(s) of ammonia. Suitable examples are ammonium chloride, ammonium sulfate, and ammonium phosphate.

It is further preferred from the viewpoint of storage stability and bleaching power that one or more inorganic alkalizing agent(s) according to group a) is sodium metasilicate.

It is further preferred from the viewpoint of bleaching power that one or more compound(s) according to group a) is/are organic alkalizing agent(s), preferably selected from, alkyl- or alkanolamines according to the general structure

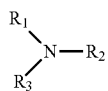

wherein R1, R2, and R3 are same or different H, from C1 to C4, C3 to C4 unsaturated alkyl, C3 to C4 branched alkyl, C1 to C4 hydroxyl alkyl, C3 to C4 unsaturated hydroxyl alkyl, C3 to C4 branched hydroxyl alkyl, with the condition that at least one of R1, R2, or R3 is different from H, and/or their mixtures, Suitable organic alkalizing agents are monoethanolamine, diethanolamine, monomethylamine, dimethylamine, trimethylamine, triethylamine, monoethylamine, diethylamine, trimethylamine, and 2-aminomethyl propanol.

The most preferred organic alkalizing agent(s) according to group a) is/are selected from monoethanolamine and/or 2-aminomethyl propanol, and/or their mixtures, and/or their salt(s).

Particularly suitable is/are mixture(s) of inorganic alkalizing agent(s) and/or their salt(s) according to group a) with organic alkalizing agent(s) and/or their salt(s) according to group a).

It is preferred from the viewpoint of alkalinity and bleaching power that the total concentration of compound(s) according to group a) is 0.25% by weight or more, preferably 0.5% by weight or more, further more preferably 1% by weight or more, calculated to the total weight of the composition.

It is preferred from the viewpoint of alkalinity and stability that the total concentration of compound(s) according to group a) is 30% by weight or less, preferably 25% by weight or less, further more preferably 20% by weight or less, calculated to the total weight of the composition.

For attaining the above-mentioned effects, it is preferred that the total concentration of compound(s) according to group a) is in the range of 0.25% to 30% by weight, preferably 0.5% to 25% by weight, more preferably 1% to 20% by weight, calculated to the total weight of the composition.

Compound(s) According to Group b)

The composition of the present invention comprises one or more bleaching compound(s) as compound(s) according to group b).

Bleaching compound(s) within the meaning of the present invention are molecules which interact with the natural melanin pigments in the keratin fibers and partially or fully destroy them so that they lose their color. Because of the interaction with the bleaching compounds, the color of the treated keratin fibers is lightened.

It is preferred from the viewpoint of strong bleaching power that that one or more compound(s) according to group b) is/are one or more persalt(s) and/or peroxy salt(s).

Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium, and ammonium persulfate.

It is preferred from the viewpoint of strong bleaching power that the total concentration of one or more persalt(s) and/or peroxy salt(s) as compound(s) according to group b) is 10% by weight or more, preferably 15% by weight or more, further more preferably 20% by weight or more, calculated to the total weight of the composition.

It is preferred from the viewpoint of keratin fiber damage that the total concentration of one or more persalt(s) and/or peroxy salt(s) as compound(s) according to group b) is 80% by weight or less, preferably 70% by weight or less, further more preferably 60% by weight or less, calculated to the total weight of the composition.

For attaining the above-mentioned effects, it is preferred that the total concentration of one or more persalt(s) and/or peroxy salt(s) as compound(s) according to group b) is in the range of 10% to 80% by weight, further more preferably 15% to 70% by weight, still further more preferably 20% to 60% by weight, still further more preferably 25% to 60% by weight, calculated to the total weight of the composition.

Compound(s) According to Group c)

The composition of the present invention comprises HC Blue 18 and/or its salt(s) as compound(s) according to group c).

It is preferred from the viewpoint of dyeing intensity that the total concentration of compound(s) according to group c) is 0.001% by weight, more preferably 0.005% by weight, further more preferably 0.01% by weight, calculated to the total weight of the composition.

It is preferred from the viewpoint of economic reasons that the total concentration of compound(s) according to group c) is 2.5% by weight or less, preferably 2% by weight or less, further more preferably 1.7% by weight or less, still further more preferably 1% by weight or less, calculated to the total weight of the composition.

For attaining the above-mentioned effects, it is preferred that the total concentration of compound(s) according to group c) is in the range of 0.001% to 2.5% by weight, preferably in the range of 0.005% to 2% by weight, more preferably in the range of 0.01% to 1.7% by weight, still further more preferably in the range of 0.01% to 1% by weight, calculated to the total weight of the composition.

Compound(s) According to Group d)

The composition of the present invention comprises tetrabromophenol blue and/or its salt(s) as compound(s) according to group d).

Commercially available tetrabromophenol blue is a mixture of hexa-, hepta-, and octabromophenolsulfonphthaleins. Thus, the general term tetrabromophenol blue as used in the present invention encompasses the aforementioned compounds and their mixtures.

It is preferred from the viewpoint of dyeing intensity that the total concentration of compound(s) according to group d) is 0.001% by weight or more, more preferably 0.005% by weight or more, further more preferably 0.01% by weight or more, still further more preferably 0.025% by weight or more, calculated to the total weight of the composition.

It is preferred from the viewpoint of commercial and cosmetic safety reasons that the total concentration of compound(s) according to group d) is 5% by weight or less, more preferably 2% by weight or less, further more preferably 1% by weight or less, still further more preferably 0.75% by weight or less, calculated to the total weight of the composition.

For attaining the above-mentioned effects, it is preferred that the total concentration of compound(s) according to group d) is in the range of 0.001% to 5% by weight, preferably in the range of 0.005% to 2% by weight, more preferably in the range of 0.01% to 1% by weight, further more preferably in the range of 0.025% to 0.75% by weight, calculated to the total weight of the composition.

It is further preferred from the viewpoint of dyeing intensity that the weight ratio of compound(s) according to group c) to compound(s) according to group d) is 1 or more, more preferably 2 or more, further more preferably 5 or more.

It is further preferred from the viewpoint of dyeing intensity and commercial reasons that the weight ratio of compound(s) according to group c) to compound(s) according to group d) is 20 or less, more preferably 15 or less, further more preferably 12 or less.

For attaining the above-mentioned effects, it is preferred that the in the range of the weight ratio of compound(s) according to group c) to compound(s) according to group d) is in the range of 1 to 20, preferably in the range of 2 to 15, more preferably in the range of 5 to 12.

Product Forms

It is preferred from the viewpoint of product stability that the composition of the present invention comprises less than 10% by weight of water, preferably less than 5% by weight of water, more preferably less than 1% by weight of water, further more preferably it is anhydrous.

The term 'anhydrous' denotes a composition that does not comprises added water. However, bound water, crystal water, or adhering air moisture is not considered as added water.

In one aspect of the present invention, the composition is a bleaching powder composition and comprises one or more pulverulent excipient as compound(s) according to group e), preferably at a total concentration of more than 30% by weight, calculated to the total weight of the composition.

It is preferred from the viewpoint of powder stability that it comprises less than 10% by weight of water, preferably less than 5% by weight of water, more preferably less than 1% by weight of water, further more preferably it is anhydrous.

The pulverulent excipient as compound(s) according to group e) may be an organic and/or an inorganic pulverulent excipient in which the compound(s) of groups a) to d) are dispersed.

Any pulverulent excipient not reacting with the dyes and the alkalizing agents is suitable for the purpose of the present invention. Suitable ones are, for example, diatomaceous earth, kaolin, bentonite, starch especially corn, tapioca, rice, wheat and potato, nylon powder, montmorillonit, gypsum, sawdust and perlite.

For this aspect of the present invention, it is preferred from the viewpoint of powder stability that the total concentration of compound(s) according to group e) is 10% by weight or more, more preferably 15% by weight or more, still more preferably 20% by weight or more, further more preferably 30% by weight or more, calculated to the total weight of the composition.

It is preferred from the viewpoint of powder stability that the total concentration of compound(s) according to group e) is 90% by weight or less, more preferably 85% by weight or less, further more preferably 80% by weight or less, calculated to the total weight of the composition.

For attaining the above-mentioned effects, it is preferred that the total concentration of compound(s) according to group e) is in the range of 10% to 90% by weight, more preferably 15 to 85% by weight, further more preferably in the range of 20% to 80% by weight, still further more preferably in the range of 30% to 80% by weight, calculated to the total weight of the composition.

In another aspect of the present invention, the composition is a bleaching paste composition comprising one or more lipophilic compound(s) being liquid at 25° C. and under atmospheric pressure as compound(s) according to group f), preferably at a total concentration of more than 30% by weight, calculated to the total weight of the composition.

It is preferred from the viewpoint of bleaching paste stability that it comprises less than 10% by weight of water, preferably less than 5% by weight of water, more preferably less than 1% by weight of water, further more preferably it is anhydrous.

Suitable compounds according to group f) are natural and/or vegetable oils, petrolatum-based compounds, linear or branched, saturated or unsaturated fatty alcohols with C12 to C22, and fatty acid esters consisting of linear or branched, saturated or unsaturated fatty acids with C12 to C22 being esterified with linear or branched primary alcohols with C3 to C12, and silicones.

Suitable natural and/or vegetable oils are olive oil, almond oil, avocado oil, wheatgerm oil, and castor oil.

Suitable petrolatum-based compounds are liquid paraffins, especially paraffinum perliquidum and paraffinum subliquidum, and mineral oil, in particular white mineral oil.

Suitable comprises fatty compounds selected from linear or branched, saturated or unsaturated fatty alcohols with C12 to C22 are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures, such as cetearyl alcohol.

Suitable examples for fatty acid esters consisting of linear or branched, saturated or unsaturated fatty acids with C12 to C22 being esterified with linear or branched primary alcohols with C3 to C18 are octyl palmitate, isocetyl palmitate, isopropyl palmitate, octyl stearate, oleyl oleate, and myristyl myristate, as well as their mixtures.

Suitably, the compositions may also comprise lipophilic ingredients such as silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; C10- to C36-fatty acid triglycerides, as well as their mixtures.

For this aspect of the present invention, it is preferred from the viewpoint of bleaching paste stability that the total concentration of compound(s) according to group f) is more than 30% by weight, more preferably 35% by weight or more, further more preferably 40% by weight or more, calculated to the total weight of the composition.

It is preferred from the viewpoint of powder stability that the total concentration of compound(s) according to group f) is 90% by weight or less, more preferably 85% by weight or less, further more preferably 80% by weight or less, calculated to the total weight of the composition.

For attaining the above-mentioned effects, it is preferred that the total concentration of compound(s) according to group f) is in the range of 30% to 90% by weight, more preferably 35 to 85% by weight, further more preferably in the range of 30% to 80% by weight, calculated to the total weight of the composition.

Thickening Polymers

It is advantageous from the viewpoint of cosmetic safety that the composition of the present invention further comprises one or more thickening polymer(s).

Preferably, the thickening polymers are selected from polymers resulting in an aqueous solution and/or aqueous dispersion at pH between 8 and 10 having a viscosity of at least 5,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as (C2-C8)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably 0.25% to 12% by weight, more preferably in the range of 0.5% to 10% by weight, calculated to the total weight of the composition.

Optional Ingredients

It is further preferred from the viewpoint of mixability of the composition of the present invention and wetting of keratin fibers that the composition of the present invention further comprises one or more surfactant(s) as compound(s) according to g), more preferably selected from non-ionic, cationic, anionic, zwitterionic/amphoteric surfactant(s).

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric/zwitterionic surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and—acetate are also suitable.

Typical cationic surfactants are cetyl trimethyl ammonium chloride, stearyl trimonium chloride, dipalmitoyl dimonium chloride, distearyl dimethyl ammonium chloride, stearamidopropyl trimonium chloride, dioleoylethyl dimethyl ammonium methosulfate, dioleoylethyl hydroxyethylmonium methosulfate.

It is preferred from the viewpoint of composition stability, wetting of keratin fibers, and ingredient dispersability that the total concentration of compound(s) according to g) is 0.1% by weight or more, preferably 0.2% by weight or more, further more preferably 0.25% by weight or more, calculated to the total weight of the composition.

It is preferred from the viewpoint of composition stability, wetting of keratin fibers, and ingredient dispersability that the total concentration of compound(s) according to g) is 5% by weight or less, preferably 4% by weight or less, further more preferably 2.5% by weight or less, calculated to the total weight of the composition.

For attaining the above-mentioned effects, it is preferred that the total concentration of compound(s) according to g) is in the range of 0.1% to 5% by weight, more preferably 0.2% to 4% by weight, further more preferably 0.2% to 2.5% by weight, calculated to the total weight of the composition.

The composition of the present invention may further comprise one or more additional direct dye different from the ones of groups c) and d). Suitable direct dyes may be selected from cationic, anionic and non-ionic dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The composition may comprise one or more additional direct dyes different from the ones of groups c) and d) at a total concentration of 0.001% to 10% by weight, calculated to the total weight of the composition.

Two-Part Composition

The present invention is also directed to a two-part bleaching and coloring composition comprising a first composition as defined above and a second aqueous composition having a pH in the range of 1 to 6 and comprising one or more oxidizing agent(s), preferably hydrogen peroxide.

The second aqueous composition preferably comprises hydrogen peroxide as an oxidizing agent. Suitable concentration range from 0.1% to 20% by weight, preferably 0.25% to 15% by weight, and more preferably 0.5% to 12% by weight, calculated to the total weight of the second aqueous composition.

The pH of the second aqueous composition preferably is in the range of 1.5 to 5, more preferably in the range of 2 to 4.5, adjusted by suitable acids and bases. It is further preferred from the viewpoint of mixability with the first composition that the second aqueous composition comprises one or more lipophilic compound(s) according to f), as laid out above for the bleaching and dyeing composition. In such a case, the second aqueous composition is an emulsion and preferably also comprises one or more surfactant(s) as compound(s) according to g), as laid out above for the dyeing composition.

First and second compositions in this aspect of the present invention are intended to be mixed directly prior to application onto keratin fibers.

Method of Dyeing

The present invention is also directed to a method for bleaching and coloring of keratin fibers, preferably human keratin fibers, more preferably human hair comprising the steps of:

i) mixing the bleaching and coloring composition as defined above with a second aqueous composition comprising one or more oxidizing agent(s), preferably hydrogen peroxide, and having a pH in the range of 1 to 6 to yield a ready-to-use composition having a pH in the range of 7 to 12, ii) applying the ready-to-use composition onto keratin fibers and leaving it for a time period of 1 to 60 min, and optionally heating the keratin fibers to a temperature in the range of 30° C. to 60° C., iii) rinsing-off the keratin fibers and optionally drying keratin fibers.

It is preferred from the viewpoint of color intensity that the pH of the ready-to-use composition as defined in step i) is in the range of 8 to 11, more preferably in the range of 8.5 to 10.5.

It is further preferred from the viewpoint of dyeing intensity and dyeing method economy that the leave-on time as defined in step ii) is in the range of 2 min to 45 min, more preferably in the range of 5 min to 40 min, further more preferably in the range of 10 min to 30 min.

Kit-of-Parts

The present invention is also directed to a kit-of-part for bleaching and coloring of keratin fibers, preferably human keratin fibers, more preferably human hair, comprising:

a first composition as defined above, a second aqueous composition having a pH in the range of 1 to 6 and comprising one or more oxidizing agent(s), preferably hydrogen peroxide, a third composition selected from an anhydrous composition comprising one or more oxidizable solvent(s), preferably selected from 2-phenoxyethanol, benzyl alcohol, and/or their mixtures, or a composition comprising one or more alkoxylated organopolysiloxane, one or more compound(s) selected from alkoxylated glyceryl ester(s) and/or optionally alkoxylated alkyl glyceryl ether(s), and/or their mixtures, at a total concentration of more than 10% by weight, calculated to the total weight of the third composition, wherein the third composition comprises less than 40% by weight of water, calculated to the total weight of the third composition.

The anhydrous third composition comprises at least one oxidizable solvent. The term 'oxidizable' denotes that the solvent is oxidized, at least partly or wholly oxidized under the conditions used for bleaching and colouring of keratin fibers.

Suitable solvents are aromatic or aliphatic alcohols and preferably comprise only one OH group in its molecule. Preferably the aromatic alcohols have a Log P value (octanol water partition coefficient) at 25° C. in the range of 0 to 2.5, preferably in the range of 0.05 to 2, more preferably 1 to 2 and most preferably 1.1 to 1.7. Suitable aromatic oxidizable alcohols are 2-phenoxyethanol, benzyl alcohol, 2-phenylethanol and 2-benzyloxyethanol. Suitable aliphatic alcohols are isopropanol, propanol, n-butanol, isobutanol, t-butanol and 1-pentanol.

The most preferred oxidizable organic alcohols from the viewpoint of dye stabilization are aromatic alcohols selected from benzyl alcohol, 2-phenoxyethanol, 2-phenylethanol. Particularly preferred is/are benzyl alcohol and/or 2-phenoxyethanol and/or 2-phenylethanol.

For the third composition comprising the alkoxylated polyorganosiloxane, it is preferred from the viewpoint of dyeing intensity that the alkoxylated non-aminated organopolysiloxane is an alkoxylated dimethicone copolymer; most preferably it is PEG/PPG-20/23 dimethicone.

It is further preferred for this third composition that one or more compound(s) selected from alkoxylated glyceryl ester(s) is PEG-7 glyceryl cocoate, PEG-9 cocoglycerides, PEG-40 hydrogenated castor oil and PEG-200 hydrogenated glyceryl palmate.

The above-mentioned third composition comprises less than 40% by weight of water.

It is preferred from the viewpoint of formulation stability that the composition comprises less than 30% by weight of water, more preferably less than 20% by weight of water, still more preferably less than 10% by weight of water, further more preferably less than 5% by weight of water, still more preferably it is anhydrous.

The following examples are to illustrate the present invention, but not to limit it.

EXAMPLES

The following compositions were prepared by mixing the powder components together and added the dyes as a last step:

|  | Ingredients | Inventive ex. 1 | Comparative ex. 1 % by weight | Comparative ex. 2 |
|---|---|---|---|---|
| Compound | a) Sodium metasilicate | 10.0 | 10.0 | 10.0 |
|  | b) Potassium persulfate | 35.0 | 35.0 | 35.0 |
|  | b) Ammonium persulfate | 10.0 | 10.0 | 10.0 |
|  | c) HC Blue 18 | 0.45 | 0.50 | — |
|  | d) Tetrabromophenol blue | 0.05 | — | 0.05 |
|  | — Xanthan gum | 0.3 | 0.3 | 0.3 |
|  | — Hydroxyethyl cellulose | 3.0 | 3.0 | 3.0 |
|  | — Tetrasodium EDTA | 2.0 | 2.0 | 2.0 |
|  | e) Diatomaceous earth |  | Ad 100.0 |  |

The powder composition from above was mixed with the following oxidizing composition in a weight ratio of 1:1.4 directly prior to application onto hair:

|  | % by weight |
|---|---|
| Hydrogen peroxide | 6.0 |
| Phosphoric acid | ad pH 3.5 |
| Water | ad 100.0 |

The resulting ready-to-use mixture had a pH around 9.5.
The following bleaching and coloring results were obtained:

| Hair type |  | Inventive ex. 1 | Comparative ex. 1 | Comparative ex. 2 |
|---|---|---|---|---|
| L6 | L* | 35.19 | 47.12 | 49.82 |
| hair | a* | −6.75 | 4.83 | −12.38 |
|  | b* | −1.72 | 14.16 | 7.20 |

Discussion of Results

Inventive ex. 1 delivered the lowest L* value indicating the strongest uptake of blue dyes in comparison to the comparative examples. It must be concluded that dyeing intensity was improved to a large degree and none of the individual dyes showed such a high degree of dye uptake.

Comparative example 1 had positive b* values indicating the undesired yellow-shift of the treated hair streaks in all cases. Comparative example 2 exhibited a strong yellow-shift on L6 hair. However, as explained above, intensity was weak as illustrated by the L* value.

Inventive example 1 showed the most balanced bleaching and coloring results, while tending to desired slightly blue shades (b* value is close to 0, but negative).

Methods

Human level 6 hair (21 cm long, 2 g per bundle) were purchased from International Hair Importers, Glendale, NY, USA. The hair was shampooed prior to treatment.

2 g of each of the compositions from above were applied onto a hair streak and left for 30 min at 50° C. Then the hair streaks were rinsed off with water, shampooed, and blow-dried. The colormetric measurements were obtained with a color-difference meter by the CIE colorimetric system (L*, a*, b*).

The following examples are within the scope of the present invention.

Example 2

|  | % by weight |
|---|---|
| Sodium metasilicate | 10.0 |
| 2-aminomethyl propanol | 5.0 |
| Potassium persulfate | 30.0 |
| Ammonium persulfate | 20.0 |
| HC Blue 18 | 0.3 |
| Tetrabromophenol blue | 0.1 |
| Light mineral oil | ad 100.0 |

The invention claimed is:

1. A bleaching and coloring composition for keratin fibers, comprising:
    one or more alkalizing agents;
    one or more bleaching compounds;
    HC Blue 18 and/or a salt thereof; and
    tetrabromophenol blue and/or a salt thereof.

2. The composition according to claim 1, wherein the one or more alkalizing agents is one or more inorganic alkalizing agents.

3. The composition according to claim 1, wherein the one or more alkalizing agents has a general structure of

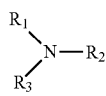

wherein $R_1$, $R_2$, and $R_3$ are same or different, and are selected from the group consisting of H, C1 to C4, C3 to C4 unsaturated alkyl, C3 to C4 branched alkyl, C1 to C4 hydroxyl alkyl, C3 to C4 unsaturated hydroxyl alkyl, and C3 to C4 branched hydroxyl alkyl, and wherein at least one of $R_1$, $R_2$, and $R_3$ is different from H.

4. The composition according to claim 1, wherein a total concentration of the one or more alkalizing agents is in a range of 0.25% to 30% by weight, calculated to the total weight of the composition.

5. The composition according to claim 1, wherein the one or more bleaching compounds is selected from the group consisting of persalts and peroxy salts.

6. The composition according to claim 1, wherein a total concentration of the HC Blue 18 is in a range of 0.001% to 2.5% by weight, calculated to the total weight of the composition.

7. The composition according to claim 1, wherein a total concentration of the tetrabromophenol blue is in a range of 0.001% to 5% by weight, calculated to the total weight of the composition.

8. The composition according to claim 1, wherein a weight ratio of the HC Blue 18 to the tetrabromophenol blue is in a range of 1 to 20.

9. The composition according to claim 1, further comprising one or more thickening polymers at a total concentration in a range of 0.1% to 15% by weight, calculated to the total weight of the composition.

10. The composition according to claim 1, comprising less than 10% by weight of water, calculated to the total weight of the composition.

11. The composition according to claim 1, wherein the composition is a bleaching powder composition and comprises one or more pulverulent excipients.

12. The composition according to claim 1, wherein the composition is a bleaching paste composition comprising one or more lipophilic compounds being liquid at 25° C. and under atmospheric pressure.

13. A two-part bleaching and coloring composition comprising a first composition according to claim 1, and a second aqueous composition having a pH in the range of 1 to 6 and comprising hydrogen peroxide as one or more oxidizing agents.

14. A method for bleaching and coloring of keratin fibers, comprising:
mixing the bleaching and coloring composition of claim 1 with a second aqueous composition comprising hydrogen peroxide as one or more oxidizing agents and having a pH in a range of 1 to 6 to yield a ready-to-use composition having a pH in a range of 7 to 12;
applying the ready-to-use composition onto the keratin fibers and leaving it for a time period of 1 to 60 min, and optionally heating the keratin fibers to a temperature in a range of 30° C. to 60° C. and
rinsing-off the keratin fibers and optionally drying the keratin fibers.

15. A kit-of-part for bleaching and coloring of keratin fibers, comprising:
a first composition of claim 1;
a second aqueous composition having a pH in the range of 1 to 6 and comprising hydrogen peroxide as one or more oxidizing agents; and
a third composition selected from the group consisting of an anhydrous composition comprising one or more oxidizable solvents selected from 2-phenoxyethanol, and benzyl alcohol, and a composition comprising one or more alkoxylated organopolysiloxane, and one or more compounds selected from alkoxylated glyceryl esters, and alkoxylated alkyl glyceryl ethers, at a total concentration of more than 10% by weight, calculated to the total weight of the third composition, and
wherein the third composition comprises less than 40% by weight of water, calculated to the total weight of the third composition.

16. The composition according to claim 1, wherein the one or more alkalizing agents is selected from the group consisting of metasilicates, carbonates, bicarbonates, and alkali or earth alkali salts thereof.

17. The composition according to claim 1, wherein the one or more alkalizing agents is sodium metasilicate.

18. The composition according to claim 1, wherein the one or more alkalizing agents is selected from the group consisting of monoethanolamine, 2-aminomethyl propanol, and salts thereof.

19. The composition according to claim 1, wherein a total concentration of the one or more bleaching compounds is in a range of 10% to 80% by weight, calculated to the total weight of the composition.

20. The composition according to claim 1, wherein a weight ratio of the HC Blue 18 to the tetrabromophenol blue is in a range of 5 to 12.

21. The composition according to claim 1, wherein the composition is anhydrous.

* * * * *